(12) United States Patent
Stampalia

(10) Patent No.: US 11,207,293 B2
(45) Date of Patent: Dec. 28, 2021

(54) THERAPEUTIC COMPOSITIONS AND USES THEREOF

(71) Applicant: Anthony Stampalia, Boca Raton, FL (US)

(72) Inventor: Anthony Stampalia, Boca Raton, FL (US)

(*) Notice: Subject to any disclaimer, the term of this patent is extended or adjusted under 35 U.S.C. 154(b) by 0 days.

(21) Appl. No.: 16/024,867

(22) Filed: Jul. 1, 2018

(65) Prior Publication Data

US 2020/0000768 A1 Jan. 2, 2020

(51) Int. Cl.

| | | |
|---|---|---|
| *A61K 31/375* | (2006.01) | |
| *A61P 9/00* | (2006.01) | |
| *A61K 31/525* | (2006.01) | |
| *A61K 31/455* | (2006.01) | |
| *A61K 31/519* | (2006.01) | |
| *A61K 31/198* | (2006.01) | |
| *A61K 31/01* | (2006.01) | |
| *A61K 9/00* | (2006.01) | |
| *A61K 31/675* | (2006.01) | |
| *A61K 31/59* | (2006.01) | |
| *A61K 33/06* | (2006.01) | |
| *A61K 36/88* | (2006.01) | |
| *A61K 31/7048* | (2006.01) | |
| *A61K 31/122* | (2006.01) | |
| *A61K 36/63* | (2006.01) | |
| *A61P 9/12* | (2006.01) | |
| *A61K 31/51* | (2006.01) | |

(52) U.S. Cl.
CPC ......... *A61K 31/375* (2013.01); *A61K 9/0053* (2013.01); *A61K 31/01* (2013.01); *A61K 31/122* (2013.01); *A61K 31/198* (2013.01); *A61K 31/455* (2013.01); *A61K 31/51* (2013.01); *A61K 31/519* (2013.01); *A61K 31/525* (2013.01); *A61K 31/59* (2013.01); *A61K 31/675* (2013.01); *A61K 31/7048* (2013.01); *A61K 33/06* (2013.01); *A61K 36/63* (2013.01); *A61K 36/88* (2013.01); *A61P 9/00* (2018.01); *A61P 9/12* (2018.01)

(58) Field of Classification Search
CPC .. A61K 31/375; A61K 9/0053; A61K 31/122; A61K 31/455; A61K 31/51; A61K 31/525; A61K 31/59; A61K 31/675; A61K 36/63
See application file for complete search history.

(56) References Cited

U.S. PATENT DOCUMENTS

| | | | |
|---|---|---|---|
| 6,555,134 B1 * | 4/2003 | Aviram | A61K 36/8962 424/456 |
| 2007/0020340 A1 * | 1/2007 | Rubin | A61K 31/05 424/523 |
| 2012/0009276 A1 * | 1/2012 | De Groote | A61K 31/565 424/639 |
| 2016/0193306 A1 * | 7/2016 | Rabovsky | A23L 33/105 424/93.3 |
| 2017/0020948 A1 * | 1/2017 | Tripp | A61K 36/82 |

OTHER PUBLICATIONS

Borek "Antioxidant Health Effects of Aged Garlic Extract" (2001), American Society for Nutritional Sciences, presented at "Recent Advance on the Nutritional Benefits Accompanying the Use of Garlic as a Supplement" held Nov. 15-17, 1998 in Newport Beach, Ca: pp. 1010S-1015S (Year: 2001).*

Hayashi et al. "L-citrulline and L-arginine supplementation retards the progression of high-cholesterol-diet-induced atherosclerosis in rabbits" 2005, PNAS, vol. 102, No. 38: 13681-13686. (Year: 2005).*

Wang et al. "Effect of Garlic on Blood Pressure: A Meta-Analysis" 2015 Journal of Clincal Hypertension, vol. 17, No. 3: 223-231 (Year: 2015).*

* cited by examiner

*Primary Examiner* — Teresa E Knight

(74) *Attorney, Agent, or Firm* — Duane Morris LLP; Gregory M. Lefkowitz

(57) ABSTRACT

The present invention discloses a composition and method of use for the general improvement of hypertension, high cholesterol, and cardiovascular health. The novel composition is comprised of thiamin (vitamin B1), vitamin B2 (as riboflavin-5'-phosphate), niacin (vitamin B3, as niacinamide), vitamin B6 (as pyridoxine hydrochloride), folic acid, vitamin C, vitamin D, calcium (as calcium carbonate), magnesium (as magnesium taurate), aged garlic extract, olive leaf extract (as 20% oleuropein), coenzyme Q10 (as ubiquinol), L-Arginine (as hydrochloride), L-Citrulline (as malate), and lycopene.

10 Claims, No Drawings

THERAPEUTIC COMPOSITIONS AND USES THEREOF

TECHNICAL FIELD

The present invention generally relates to therapeutic compositions which help reduce blood pressure, lower cholesterol, and promote a healthy cardiovascular system.

BACKGROUND

Heart disease has been the leading cause of death in the United States for many years. In fact, heart disease accounts for over 600,000 deaths each year.

While there are many factors at hand, perhaps the most relevant indication of heart disease is chronic hypertension. Chronic hypertension occurs when the arteries experience a long-term increase in blood pressure, leading to a multitude of residual effects. These can include coronary artery disease, stroke, heart failure, atrial fibrillation, peripheral vascular disease, vision loss, chronic kidney disease, and dementia.

Another significant risk factor is hypercholesterolemia (high cholesterol), caused by high levels of cholesterol in the bloodstream as a consequence of poor diet, obesity, or inherent genetic factors. Longstanding elevations of serum cholesterol can lead to atherosclerosis and the formation of atheromatous plaques in the arteries. If untreated, an artery may become suddenly blocked, resulting in a heart attack.

To mitigate risk, it is recommended that high risk candidates make dietary and lifestyle changes as soon as possible to reduce the probability of heart disease. Dietary restrictions are heavily debated as new research further exemplifies the complexity of the human biological system specific to each individual. Lowering stress and engaging in exercise are most commonly recommended.

While medications exist to lower cholesterol and improve cardiovascular function, they are still ineffective in eliminating risk and have a variety of potential side effects, hence, dietary, and lifestyle changes are commonly prescribed in addition to any medication. Historically, many medications have focused on the management of blood lipids. It is also known that inflammation can occur in conjunction with cardiovascular disease at the early stages, management of the inflammatory response is not a focus of treatment. Inflammatory intervention may be useful as a prophylactic measure in the treatment of heart disease before a heart attack occurs.

It is well known that a variety of vitamins and natural compounds are useful in promoting a healthy cardiovascular system. However, these are typically formulating in an inconsiderate manner without accounting for interactions of the compounds at a range of dosing protocols.

It can be seen that an improvement in the arts related to the promotion of a healthy cardiovascular system is needed in the current arts. One advancement is provided in the various embodiments described herein.

SUMMARY OF THE INVENTION

This summary is provided to introduce a variety of concepts in a simplified form that is further disclosed in the detailed description of the invention. This summary is not intended to identify key or essential inventive concepts of the claimed subject matter, nor is it intended for determining the scope of the claimed subject matter.

Embodiments herein provide for a composition useful in treating or improving hypertension, high cholesterol, and cardiovascular health overall. The composition utilizes mechanisms of action including centrally acting alpha agonists, beta blockers, calcium channel blockers, vasodilators, diuretics, and inhibitors of the renin-angiotensin system. A preferred composition includes thiamin (vitamin B1), vitamin B2 (as riboflavin-5'-phosphate), niacin (vitamin B3, as niacinamide), vitamin B6 (as pyridoxine hydrochloride), folic acid, vitamin C, vitamin D, calcium (as calcium carbonate), magnesium (as magnesium taurate), aged garlic extract, olive leaf extract (as 20% oleuropein), coenzyme Q10 (as ubiquinol), L-Arginine (as hydrochloride), L-Citrulline (as malate), and lycopene. The composition is formulated and provided as a supplement to be administrated daily via the oral route.

In one aspect, a method for improving at least one risk factor related to cardiac disease in a subject includes administering to the subject a sufficient amount of a composition. The composition is administered each day orally and is comprised of thiamin (vitamin B1), vitamin B2 (as riboflavin-5'-phosphate), niacin (vitamin B3, as niacinamide), vitamin B6 (as pyridoxine hydrochloride), folic acid, vitamin C, vitamin D, calcium (as calcium carbonate), magnesium (as magnesium taurate), aged garlic extract, olive leaf extract (as 20% oleuropein), coenzyme Q10 (as ubiquinol), L-Arginine (as hydrochloride), L-Citrulline (as malate), and lycopene.

Moreover, in accordance with a preferred embodiment of the present invention, other aspects, advantages, and novel features of the present invention will become apparent from the following detailed description in conjunction with the drawings.

DETAILED DESCRIPTION

The specific details of the single embodiment or variety of embodiments described herein are to the described formula. Any specific details of the embodiments are used for demonstration purposes only and not unnecessary limitations or inferences are to be understood therefrom.

Any reference to "invention" within this document is a reference to an embodiment of a family of inventions, with no single embodiment including features that are necessarily included in all embodiments, unless otherwise stated. Furthermore, although there may be references to "advantage's" provided by some embodiments, other embodiments may not include those same advantages, or may include different advantages. Any advantages described herein are not to be construed as limiting to any of the claims.

In one aspect, this invention relates to a multi-component formula, where each component has anti-inflammatory activity and/or antioxidant activity. The components each have a specific mode of action in the body, and their anti-inflammatory and/or antioxidant effects are complimentary. The components each have their characteristic bioavailability and metabolism. It is important to note that the compositions covered in this invention optimize effectiveness by combining components with complementary actions. Components of the formulas also have different pharmacokinetic properties. Combining select components enhances their overall effectiveness.

In another aspect, the invention provides a method of improving at least one risk factor in a subject possessing said risk factor or risk factors comprising administering to said subject an effective amount of any composition presented herein, wherein: the risk factors are selected from the group consisting of hypertension, elevated low-density lipoprotein (LDL) cholesterol levels, low high-density lipoprotein (HDL) cholesterol levels, elevated triglycerides, and elevated body mass index (BMI), such that at least one of said risk factors is improved.

In any of the embodiments presented herein, the subject referred to herein may or may not suffer from one or more of diseases or disorders selected from the group consisting of cardiovascular disease, atherosclerosis, heart failure, hypercholesterolemia, and inflammation associated with pain In another aspect, the invention provides a method of treating cardiovascular disease in a subject identified as suffering from a cardiovascular disease comprising the administration to the subject an effective amount of any composition presented herein, such that the cardiovascular disease is improved. In specific instances, the treatment reduces one or more parameters selected from the group consisting of blood pressure, atherosclerosis, platelet aggregation, total cholesterol levels, C-reactive protein. BMI, triglycerides, and LDL cholesterol levels.

As used herein, the term "treating" or "improving" a disorder encompasses preventing, ameliorating, mitigating and managing the disorder and/or conditions that may cause the disorder. The terms "treating" and "treatment" refer to a method of alleviating or abating a disease and its attendant symptoms. In accordance with the present invention "treating" includes preventing, blocking, inhibiting, attenuating, protecting against, modulating, reversing the effects of and reducing the occurrence of, e.g., the harmful effects of a disorder.

As used herein, as "extract" is a preparation of constituents of a material (e.g., garlic), including, for example, solvent extracts, concentrated forms of said constituents, concentrated solvent extracts, isolated chemical compounds or mixtures thereof.

Compounds (e.g., isolated compounds, compounds within extracts, compounds fractionated from extracts) of the invention can be made by means known in the art of organic synthesis. Methods for optimizing reaction conditions, if necessary minimizing competing by-products are known in the art.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

In some embodiments, a carrier may be utilized. Some examples of substances which can serve as pharmaceutical carriers are sugars, such as lactose, glucose, and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cottonseed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline, and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants, and preservatives, can also be present.

In a preferred embodiment, the composition of the invention herein is administered orally with or without the addition of a foodstuff. The composition is preferably administered in a single dose in the morning. To achieve the maximum benefit, the composition is taken on a regularly scheduled 24-hour cycle, such that the composition is self-administered once daily. It is noted that it is essential to maintain a continuous dosing schedule independent of self-analysis of one's condition. In one dosing protocol, the subject self-administers the composition as described herein orally upon waking in the morning. This continues each morning until a medical practitioner recommends changes.

It is noted that benefits of the composition herein may, or may not onset immediately be following administration. It may require a period, such as one month before benefits are realized, whether anecdotally or analytically.

The composition and alternatives thereof are presented herein as a preferred embodiment. Thiamin (Vitamin B1) is known to provide a modest decrease in blood pressure in subjects with conditions including diabetes mellitus, obesity, cirrhosis, and alcoholism where thiamine is deficient. Thiamine acts through the renin-aldosterone-angiotensin system and is an essential vitamin involved in glucose production.

Vitamin B2 (riboflavin) is provided with the composition in a preferred embodiment. Vitamin B2 supplementation has been shown to have a possible benefit for cardiovascular health in subjects having two copies of gene MTHFR 677TT and abnormally elevated homocysteine due to defects in folate metabolism. In these subjects, blood pressure and homocysteine are decreased when Vitamin B2 supplementation is administered.

Niacin (Vitamin B3) as niacinamide is effective for normalizing lipids and can increase HDL-C (high-density lipoprotein-cholesterol) levels and can reduce LDL-C (low-density lipoprotein cholesterol) levels. Furthermore, it is shown that triglyceride levels are decreased upon niacin supplementation. Niacin has also been shown to decrease the risk of myocardial infarction.

Vitamin B6 (pyridoxine) is a known angiotensin receptor blocker, calcium channel blocker, and also reduces sympathetic nervous system activity.

Folic acid is beneficial for blood flow and cardiac disease by reducing homocysteine levels in subjects with coronary artery disease. Folic acid is also known to have high antioxidant activity.

Vitamin C (as calcium pantothenate) is presented to have the capacity to reduce C-reactive protein and increase oxidant enzymes. Vitamin C is an angiotensin-receptor-blocker, a calcium channel blocker, and a direct vasodilator. It is also known that vitamin C reduces sympathetic nervous system activity.

Vitamin D (as D3 Cholecalciferol) is known to decrease the risk of cardiovascular disease and has a cardioprotective activity when given as a supplement. Vitamin D is also known as a renin inhibitor and can, therefore, reduce blood pressure.

Calcium (as calcium carbonate) is provided with the composition. Low dietary calcium may be associated with increased arterial stiffness. The presence of calcium in the arteries is predictive of cardiovascular disease, which can be assessed by a coronary artery calcium score. Calcium is also known as a direct vasodilator.

Magnesium (as magnesium taurate) is provided as a calcium channel blocker and can reduce blood pressure.

Magnesium is also known to reduce C-reactive protein in addition to triglyceride levels. Further, magnesium can increase chylomicron clearance and HDL-C. Upon supplementation, magnesium has been shown to improve glucose metabolism and is related to cardiovascular health.

Aged garlic extract is known to reduce total cholesterol and LDL-C and can increase HDL-L and triglyceride levels. Garlic has also been shown to reduce angiotensin converting enzyme activity, arterial stiffness, and platelet aggregation. Aged garlic extract has also been shown to be a vasodilator and can reduce blood pressure by 8-10%. It has been shown that aged garlic extract can increase nitric oxide resulting in further vasodilation. Antioxidant enzyme profiles have also been shown to increase.

Garlic administration in patients with coronary artery disease often increase physical performance and can reduce heart rate in these patients. Commonly, statins are prescribed as an inhibitor of HMG-CoA, for which aged garlic extract is known to have similar inhibitory properties.

Olive leaf extract (as 20% Oleuropein) has been shown to decrease blood pressure and is comparable to captopril. Oleanic acid within the olive leaf extract is an angiotensin-converting enzyme inhibitor (ACEI). It is known that olive leaf extract is an antioxidant, acting to increase the activity of the enzyme glutathione peroxidase. The polyphenolic content of olive oil shows broad cardioprotective qualities and decreases total cholesterol.

Coenzyme Q10 (as ubiquinol) is provided as a known blood flow and endothelial protectant. Ubiquinol has been shown to decrease blood pressure and increase levels of antioxidant enzymes. To benefit lifestyle changes, ubiquinol has been shown to increase exercise capacity in patients following a myocardial infarction.

L-Arginine (as hydrochloride) and L-Citrulline (as malate) are provided to increase blood flow while decreasing blood pressure. Nitric oxide is also increased upon their supplementation while mediating a wide variety of conditions. L-Citrulline is an alternative to L-Arginine due to it circumventing the poor absorption and then converting to L-Arginine in the kidneys.

Lycopene is known to have cardioprotective activity in humans and effects cardiac, endothelial, and vascular functions.

A non-limiting example of the composition with ingredients is shown in the following Table 1. The composition is designed to reduce hypertension, reduce high serum cholesterol, and promote a healthy cardiovascular system.

TABLE 1

| | amount per serving | % daily value |
|---|---|---|
| Thiamine (Vitamin B1) | 1.5 mg | 100% |
| Vitamin B2 (as riboflavin-5'-phosphate) | 1.7 mg | 100% |
| Niacin (Vitamin B3, as niacinamide) | 10 mg | 50% |
| Vitamin B6 (as pyridoxine hydrochloride) | 2 mg | 100% |
| Folic Acid | 400 mcg | 100% |
| Vitamin C (as calcium carbonate) | 1000 mg | 1000% |
| Vitamin D (as D3 Cholecalciferol) | 400 i.u. | 100% |
| Calcium (as calcium carbonate) | 200 mg | 20% |
| Magnesium (as magnesium taurate) | 400 mg | 100% |

TABLE 1-continued

| | amount per serving | % daily value |
|---|---|---|
| Aged Garlic Extract | 480 mg | NA |
| Olive Leaf Extract (20% Oleuropein) | 500 mg | NA |
| Coenzyme Q10 (as ubiquinol) | 100 mg | NA |
| L-Arginine (as hydrochloride) | 650 mg | NA |
| L-Citrulline (as malate) | 1350 mg | NA |
| Lycopene | 50 mg | NA |

Table 1 above illustrates the preferred amount per serving for each ingredient of the composition. The novel combination of these vitamins, herbs, minerals, and amino acids exude antihypertensive effects in patients both as a potential treatment for a variety of conditions as well as a prophylactic to aid in the prevention of these conditions. As formulated, the novel composition has additive and synergistic benefits not seen in the current arts. Effects are the reduction of blood pressure (hypertension), decreased inflammation, decreased oxidative stress, and favorable vascular immune function.

In another embodiment. Table 2 illustrates preferred ranges of the composition to reduce hypertension, reduce high serum cholesterol, and promote a healthy cardiovascular system. This example is intended to be non-limiting. Each range is intended to encompass a therapeutically effective amount of the compound. The term "therapeutically effective amount" refers to that amount of the compound being administered sufficient to prevent the development of or alleviate to some extent one or more symptoms of the condition or disorder being treated.

TABLE 2

| | Preferred Range |
|---|---|
| Thiamine (Vitamin B1) | 0.2-4 mg |
| Vitamin B2 (as riboflavin-5'-phosphate) | 0.2-30 mg |
| Niacin (Vitamin B3, as niacinamide) | 1-400 mg |
| Vitamin B6 (as pyridoxine hydrochloride) | 1-4 mg |
| Folic Acid | 100-1000 mcg |
| Vitamin C (as calcium carbonate) | 1000-4000 mg |
| Vitamin D (as D3 Cholecalciferol) | 100-1000 i.u. |
| Calcium (as calcium carbonate) | 20-500 mg |
| Magnesium (as magnesium taurate) | 200-800 mg |
| Aged Garlic Extract | 4-800 mg |
| Olive Leaf Extract (20% Oleuropein) | 100-800 mg |
| Coenzyme Q10 (as ubiquinol) | 10-250 mg |
| L-Arginine (as hydrochloride) | 300-1000 mg |
| L-Citrulline (as malate) | 500-2000 mg |
| Lycopene | 10-1500 mg |

As provided above, synergistic effects of the composition are notably crucial to producing desired anti-inflammatory, cardioprotective, and cholesterol-lowering effects. In a preferred embodiment, the composition is provided without grape seed extract. It is known that grape seed extract and Vitamin-C can lead to an increase in blood pressure as referenced in Warn N C et al. *The combination of vitamin C and grape-seed polyphenols increases blood pressure: a randomized, double-blind, placebo-controlled trial. J. Hypertens*, 23(2):427-434, February 2005. In such, grape seed extract can be detrimental to the cardioprotective properties of the composition.

Table 3 illustrates mechanisms of action for each compound provided in the composition.

TABLE 3

|  | Functional class of antihypertensives |
| --- | --- |
| Aged Garlic Extract<br>Coenzyme Q10<br>Vitamin C<br>Vitamin B6 | Centrally acting alpha agonists (decrease sympathetic outflow) |
| Vitamin C<br>Aged Garlic Extract<br>Magnesium<br>Vitamin B6 | Beta Blockers<br>Calcium Channel Blockers |
| Aged Garlic Extract<br>Arginine<br>Calcium<br>Magnesium<br>Vitamin C | Vasodilators |
| Coenzyme Q10<br>Vitamin C<br>Vitamin B6 | Diuretics |
| Aged Garlic Extract<br>Olive Leaf Extract<br>Aged Garlic Extract<br>Coenzyme Q10<br>Vitamin C<br>Vitamin B6 | Angiotensin-converting enzyme inhibitors<br>Angiotensin Receptor Blockers |
| Vitamin D | Direct Renin Inhibitors |

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A therapeutic composition comprising:
  a. 0.2-4 mg of thiamin;
  b. 0.2-30 mg of vitamin B2;
  c. 1-19 mg of niacin;
  d. 1-4 mg of vitamin B6;
  e. 100-1000 mcg of folic acid;
  f. 1000-4000 mg of vitamin C;
  g. 100-1000 I.U. of vitamin D;
  h. 20-500 mg of calcium;
  i. 200-800 mg of magnesium;
  j. 400-800 mg of aged garlic extract;
  k. 500-800 mg of oleuropein;
  l. 10-250 mg of coenzyme Q10;
  m. 550-750 mg of L-arginine;
  n. 1250-1450 mg of L-citrulline; and
  o. 40-70 mg of lycopene.

2. The composition of claim 1, wherein the therapeutic composition is administered orally.

3. The composition of claim 1, wherein the therapeutic composition is administered once per day.

4. A composition comprising:
  a. 1.25-1.75 mg of thiamin;
  b. 1.5-2.0 mg of vitamin B2;
  c. 9-11 mg of niacin;
  d. 1.5-2.5 mg of vitamin B6;
  e. 350-450 mcg of folic acid;
  f. 950-1050 mg of vitamin C;
  g. 350-450 I.U. of vitamin D;
  h. 175-225 mg of calcium;
  i. 350-450 mg of magnesium;
  j. 440-520 mg of aged garlic extract;
  k. 450-550 mg of oleuropein;
  l. 90-110 mg of coenzyme Q10;
  m. 600-700 mg of L-arginine;
  n. 1300-1400 mg of L-citrulline; and
  o. 40-60 mg of lycopene.

5. The composition of claim 4, wherein the oleuropein is isolated, extracted, or concentrated from olive water, olive pulp, olive leaf, olive oil, or a synthetic source.

6. The composition of claim 4, wherein the composition is administered orally.

7. The composition of claim 4, wherein the therapeutic composition is administered once per day.

8. A method of improving hypertension in a subject, the method comprising administering to a subject a composition comprising:
  a. 0.2-4 mg of thiamin;
  b. 0.2-30 mg of vitamin B2;
  c. 1-19 mg of niacin;
  d. 1-4 mg of vitamin B6;
  e. 100-1000 mcg of folic acid;
  f. 1000-4000 mg of vitamin C;
  g. 100-1000 I.U. of vitamin D;
  h. 20-500 mg of calcium;
  i. 200-800 mg of magnesium;
  j. 400-800 mg of aged garlic extract;
  k. 500-800 mg of oleuropein;
  l. 10-250 mg of coenzyme Q10;
  m. 550-750 mg of L-arginine;
  n. 1250-1450 mg of L-citrulline; and
  o. 40-70 mg of lycopene.

9. The method of claim 8, wherein the composition is administered orally once per day.

10. The method of claim 8, wherein the composition comprises:
  a. 1.25-1.75 mg of thiamin;
  b. 1.5-2.0 mg of vitamin B2;
  c. 9-11 mg of niacin;
  d. 1.5-2.5 mg of vitamin B6;
  e. 350-450 mcg of folic acid;
  f. 950-1050 mg of vitamin C;
  g. 350-450 I.U. of vitamin D;
  h. 175-225 mg of calcium;
  i. 350-450 mg of magnesium;
  j. 440-520 mg of aged garlic extract;
  k. 450-550 mg of oleuropein;
  l. 90-110 mg of coenzyme Q10;
  m. 600-700 mg of L-arginine;
  n. 1300-1400 mg of L-citrulline; and
  o. 40-60 mg of lycopene.

* * * * *